United States Patent [19]

Terskikh et al.

[11] Patent Number: 5,672,513
[45] Date of Patent: Sep. 30, 1997

[54] CARCINO-EMBRYONIC ANTIGEN DERIVATIVES LACKING THE CARBOXYL TERMINAL END

[75] Inventors: Alexey Terskikh, Lausanne, Switzerland; André Pèlegrin, Montpellier, France; Jean-Pierre Mach, Lausanne, Switzerland

[73] Assignee: Roche Diagnostic Systems, Inc., Branchburg, N.J.

[21] Appl. No.: 217,299

[22] Filed: Mar. 23, 1994

[30] Foreign Application Priority Data

Mar. 25, 1993 [EP] European Pat. Off. ............. 93810214

[51] Int. Cl.$^6$ .................... G01N 33/574; C07K 14/47; C07K 14/82
[52] U.S. Cl. .................... 436/64; 530/395; 530/828
[58] Field of Search .................... 530/395, 828; 436/64

[56] References Cited

U.S. PATENT DOCUMENTS

| | | |
|---|---|---|
| 3,663,684 | 5/1972 | Freedman et al. |
| 4,879,213 | 11/1989 | Fox et al. |
| 5,274,087 | 12/1993 | Barnett et al. |

FOREIGN PATENT DOCUMENTS

| | | |
|---|---|---|
| 263 933 | 4/1988 | European Pat. Off. |
| 346 710 | 12/1989 | European Pat. Off. |
| 2095728 | 6/1971 | France |

OTHER PUBLICATIONS

Bowie et al. Science 247:1306–1310 1990.
Burgess et al. J. Cell Biol. 111:2129–38 Nov. 1990.
Lazar et al. Mol. Cell Biol. 8(3):1247–52. Mar. 1988.
Shively, et al., CRC Critical Reviews in Oncology/Hematology 2: pp. 355–399 (1995).
Mach, et al., Cancer 3: pp. 685–693, (1991).
Zimmermann, et al., Proc. Natl. Acad. Sci. USA, 84, pp. 2960–2964, (1987).
Beauchemin, et al., Mol. Cell. Biol., 7: pp. 3221–3230, (1987).
Oikawa, et al., Biochem. Biophys Res. Commun., 146: pp. 464–469 (1987).
Hefta., et al., Proc. Natl. Acad. SCI., USA 85: pp. 4648–4652 (1988).
Caras, et al., Science, 238 pp. 1280–1283 (1987).
Hefta, et al., Cancer Research, 50: pp. 2397–2403, (Apr. 15, 1990).
Morinaga, et al., Bio/Tech. 2: pp. 636–639, (Jul. 1984).
Hemperly, et al., Proc. Natl. Acad. Sci., USA 83: pp. 9822–9826 (1986).
Kuroki, et al., Immunol. Invest. 21: pp. 241–257 (1992).
Udenfriend, et al., Cell Biol. Internatl. Reports, 15: No. 9, pp. 739–759 (1991).
Kuroki, et al., Jpn. J. Cancer Res. 83: pp. 505–514, (May 1992).

Hammarstrom, et al., Cancer Res. 49: pp. 4852–4858 (Sep. 1, 1989).
Carrel, et al., Cancer Research, 36: pp. 3978–3984 (Nov. 1976).
Caignard, et al., Int. J. Cancer: 36: pp. 273–279 (1985).
Rutzky, et al., Cancer Research 40: pp. 1443–1448 (1980).
Pelegrin, et al., Int. J. Cancer, 52: pp. 110–119 (1992).
Hauch et al., Cancer Research 51: pp. 3526–3533 (1991).
Zimmermann, et al., Cancer Research, 48: pp. 2550–2554 (May 1, 1988).
Martin, et al., Int. J. Cancer, 32: pp. 623–627 (1983).
Buchegger, et al., Immunology Letters, 5: pp. 85–91 (1982).
Buchegger, et al., Int. J. Cancer, 33: pp. 643–649 (1984).
Fritsche, et al., Immunochemistry, 14: pp. 119–127 (1977).
Pelegrin, et al., Cancer, 67: pp. 2529–2537 (1991).
Lisanti, et al., Cell Bio. Intl. Reports 15: pp. 1023–1049 (1991).
Mach, et al., Nature, 248: pp. 704–706 (Apr. 19, 1974).
Krupey, et al., Immunochemistry, 9: pp. 617–622 (1972).
Buchegger, et al., J. of Nuclear Medicine 31: pp. 1035–1045 (Jun. 1990).
Hemperly, et al., Proc. Natl. Acad. Sci., USA 83: pp. 9822–9826, (Dec. 1986).
Hammarstrom, et al., Cancer Research 49: pp. 4852–4858, (Sep. 1, 1989).
Morrow, J. F., Methods in Enzymology 68: pp. 3–24, (1979).
Graham, et al., Virology 54: 536–539, (1973).
Towbin, et al., Proc. Natl. Acad. Sci., USA, 76: pp. 4350–4354, (1979).

(List continued on next page.)

Primary Examiner—Anthony C. Caputa
Attorney, Agent, or Firm—George W. Johnston; Dennis P. Tramaloni; Bruce A. Pokras

[57] ABSTRACT

The present invention provides recombinant CEA glycoproteins and methods for their production. These recombinant CEA glycoproteins s lack the C-terminal 26 amino acids which are present in natural CEA and are characterized in that they are free from cross-reactive CEA-like antigens, antigenically indistinguishable from the soluble form of CEA shed from tumor cells, and devoid of the ethanolamine which is present at the C-terminus of natural CEA, and also devoid of the additional amino acids which may be attached to the natural CEA through said ethanolamine. Said recombinant CEA glycoproteins s preferably have the amino acid sequence SEQ ID NO: 1. The CEA glycoproteins s of the invention may be used as reagents in an immunoassay for the diagnosis of neoplastic diseases. The invention also relates to a DNA encoding said recombinant CEA glycoprotein, such as the DNA having the nucleotide sequence SEQ ID NO: 2 or a functional equivalent sequence thereof. The present invention also relates to recombinant vectors comprising said DNA, which recombinant vector is capable of directing the expression of said DNA in a compatible host cell, and to transformed host cells containing such a recombinant vector. The recombinant CEA glycoprotein of the present invention, preferably integrated in a test-kit, may be used for determining the presence of tumor cells in a sample of body fluid.

3 Claims, 4 Drawing Sheets

OTHER PUBLICATIONS

"Monoclonal Antibodies To Carcinoembyronic Antigen: A Systematic Analysis Of Antibody Specificities By Using Related Normal Antigens And Evidence For Allotypic Determinants On Carcinoembryonic Antigen", Kuroki et al, The Journal of Immunology, vol. 133, No. 4, pp. 2090–2097 (1984).

"Epitope Mapping Of The Carcinoembryonic Antigen With Various Related Recombinant Proteins Expressed In Chinese Hamster Ovary Cells And 25 Distinct Monoclonal Antibodies", Ikeda et al, Molecular Immunololgy, vol. 29, No. 2. pp. 229–240, (1992).

Fredic, et al., Biochem. & Biophysical Res. Comm., 155: pp 794–800, Sep. 15, 1988.

Japanese abstract, Oikawa Shinzo, et al. JP–A–63 177 794 Jul. 21, 1988.

Terskikh, et al., Mol. Imm., 30: pp. 921–253.

CARCINO-EMBRYONIC ANTIGEN DERIVATIVES LACKING THE CARBOXYL TERMINAL END

BACKGROUND OF THE INVENTION

The present invention relates to derivatives of the carcinoembryonic antigen (CEA).

Carcinoembryonic antigen (CEA) is one of the most studied human tumor markers and is widely used in the diagnosis of neoplastic diseases, such as colorectal cancer. Thus, e.g., when the serum levels of CEA are elevated in a patient, a drop of CEA levels after surgery means that the resection of the tumor was successful. On the other hand, a subsequent rise in serum CEA levels after surgery indicates that metastases of the original tumor may have formed or that new primary tumors have grown. For a review see Shively J. E. and Beatty J. D., "CEA-related antigens: molecular biology and clinical significance", Crit. Rev. Oncol. Hematol., 2, 355–399 [1985]; and Mach J. -P., Pèlegrin A. and Buchegger F., "Imaging and therapy with monoclonal antibodies in non-hematopoietic tumors", Curr. Opin. Immunol., 3, 685–693 [1991].

The complete cDNA sequence encoding the CEA protein cedes for a polypeptide of 702 amino acids consisting of a 34 amino acid residues long leader peptide, a 108 amino acid residues long $NH_2$-terminal domain, three homologous repeating domains of 178 amino acid residues and a hydrophobic C-terminal domain of 26 amino acid residues (Zimmermann W., Ortlieb B., Friedrich R. and von Kleist S., "Isolation and characterization of cDNA clones encoding the human carcinoembryonic antigen reveal a highly conserved repeating structure", Proc. Natl. Acad. Sci. U S A, 84, 2960–2964 [1987]; Beauchemin N., Benchimol S., Cournoyer D., Fuks A. and Stunners C. P. "Isolation and characterization of full-length functional cDNA clones for human carcinoembryonic antigen", Mol. Cell. Biol., 7, 3221–3230 [1987]; Oikawa S., Kosaki G. and Nakazato H., "Molecular cloning of a gene for a member of carcinoembryonic antigen (CEA) gene family; signal peptide and N-terminal domain sequences of nonspecific crossreacting antigen (NCA)", Biochem. Biophys. Res. Commun., 146, 464–469 [1987]). The 34 amino acid residues long leader peptide is cleaved from the precursor CEA polypeptide in the process of the transfer through the endoplasmatic reticulum membrane.

The hydrophobic C-terminal domain is also missing in the mature membrane-bound CEA glycoprotein. It has been shown that CEA is attached to the membrane through a phosphatidylinositol-glycan ("PI-G") tail covalently linked through ethanolamine to the C-terminal residue of mature CEA (Hefta S. A., Hefta L. J., Lee T. D., Paxton R. J. and Shively J. E., "Carcinoembryonic antigen is anchored to membranes by covalent attachment to a glycosylphosphatidylinositol moiety: identification of the ethanolamine linkage site", Proc. Natl. Acad. Sci. U S. A. 85, 4648–4652 [1988]). It is generally assumed that CEA is processed post-translationally to remove the hydrophobic C-terminal domain with subsequent addition of a PI-G anchor to the last amino acid of the third repeated domain. The PI-G tail can be cleaved by phosphatidylinositol-specific phospholipase C releasing the membrane-bound form of CEA. The soluble form of CEA formed in this way always comprises the ethanolamine residue coupled to the carboxy-terminus of the last amino acid sequence present in the mature form of CEA (i.e. the carboxy-terminus of the last amino acid of the third repeated domain) and possibly some fragment of the PI-G tail.

It has been suggested (Caras I. W., Weddell G. N., Davitz M. A., Nussenzweig V. and Martin D. W., Jr., "Signal for attachment of a phospholipid membrane anchor in decay accelerating factor", Science, 238, 1280–1283 [1987]; Hefta L. J., Schrewe H., Thompson J. A., Oikawa S., Nakazato H. and Shively J. E., "Expression of complementary DNA and genomic clones for carcinoembryonic antigen and nonspecific cross-reacting antigen in Chinese hamster ovary and mouse fibroblast cells and characterization of the membrane-expressed products", Cancer Res. 50, 2397–2403 [1990]; Hemperly J. J., Edelman G. M. and Cunningham B. A. "cDNA clones of the neural cell adhesion molecule (N-CAM) lacking a membrane-spanning region consistent with evidence for membrane attachment via a phosphatidylinositol intermediate", Proc. Natl. Acad. Sci. U S A 83, 9822–9826 [1986]) that the COOH-terminal domain of PI-G anchored proteins is important for their correct targeting and attachment to the cell surface. Complete or partial deletion of the hydrophobic domain can result in the secretion of mutant proteins into the medium (Udenfriend S., Micanovic R. and Kodukula K., "Structural requirements of a nascent protein for processing to a PI-G anchored form: studies in intact cells and cell-free systems", Cell Biol. Int. Rep. 15, 739–759 [1991]).

The standard CEA reference presently used is generally isolated from extracts of human tumors. This CEA appears to be shed from the cell surface of tumors by cleavage of the PI-G anchor (Kuroki M., Murakami M., Wakisaka M., Ikeda S., Oikawa S., Oshima T., Nakazato H., Kosaki G. and Matsuoka Y., "Immunoreactivity of recombinant carcinoembryonic antigen proteins expressed in Escherichia coli", Immunol. Invest. 21, 241–257 [1992]). The disadvantage of the CEA isolated from human tumor extracts is that it may contain cross-reactive CEA-like antigens which may interfere with an immunoassay of the CEA released by tumors. It is known that these CEA-like antigens are elevated in many non-cancerous conditions, such as, e.g., in inflammatory liver diseases and in smokers. Efforts to overcome the problem caused by interfering CEA-like antigens led to the cloning of the DNA encoding CEA. In EP-A-263,933 various nucleic acid sequences ceding for CEA peptide sequences are disclosed.

Efforts to express different domains of the CEA molecule in bacteria showed that the CEA domains expressed in bacteria had a lower antigenicity, presumably due to incomplete folding (Kuroki M., Murakami M., Wakisaka M., Krop Watorek A., Oikawa S., Nakazato H., Kosaki G. and Matsuoka Y., "Epitopes predominantly retained on the carcinoembryonic antigen molecules in plasma of patients with malignant tumors but not on those in plasma of normal individuals", Jpn. J. Cancer Res. 83, 505–514 [1992]).

As an alternative to the use of human tumor extracts, it has been proposed to purify CEA from the culture medium from human cancer cell lines. It has been found however, that the complete mature form of CEA is not actively secreted, but only shed in low mounts (see below) in the culture medium of colon cancer carcinoma cell lines. One solution to overcome the problem of the low-level expression was to prepare fragments of CEA. However, quite obviously the fragments often do not comprise all important epitopes which are present in CEA, i.e., the epitopes generally known as GOLD 1–5 described by Hammarstrom et al., "Antigenic sites in carcinoembryonic antigen", Cancer Res. 49, 4852–4858 [1989].

SUMMARY OF THE INVENTION

The problem to be solved by the present invention was therefore to provide a CEA derivative which is free from cross-reactive CEA-like antigens, is antigenically indistingiushable from the soluble form of CEA shed from tumor cells, i.e., comprises all important epitopes of the CEA protein, and on the other hand is secreted in high amounts by a recombinant host.

It has now been found that a recombinant cDNA encoding CEA which lacks the 3' region encoding the 26 amino acid hydrophobic domain is capable of providing a CEA derivative which fulfils the requirements outlined above. Upon transfection of the said cDNA into, a suitable host cell, such as a rat or a human carcinoma cell, a 50- to 100-fold higher level of secretion of a fully immunogenic CEA glycoprotein into the culture medium is obtained.

DETAILED DESCRIPTION OF THE INVENTION

Figure 1:
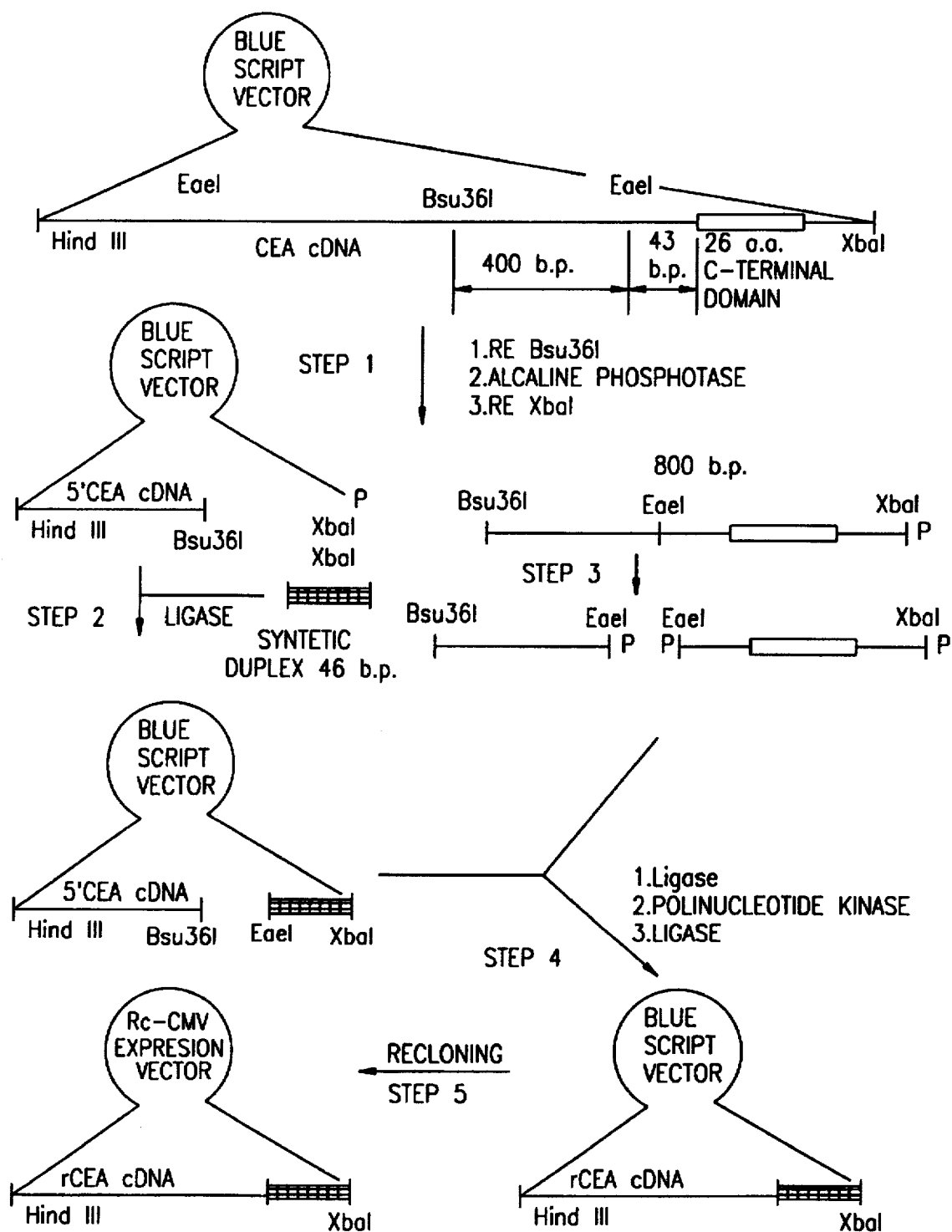
FIG. 1: Schematic outline of the construction of an exemplary recombinant truncated CEA cDNA in accordance with the present invention. The black box represents the deleted hydrophobic domain. Phosphorylated ends are marked by P.
Figure 2:
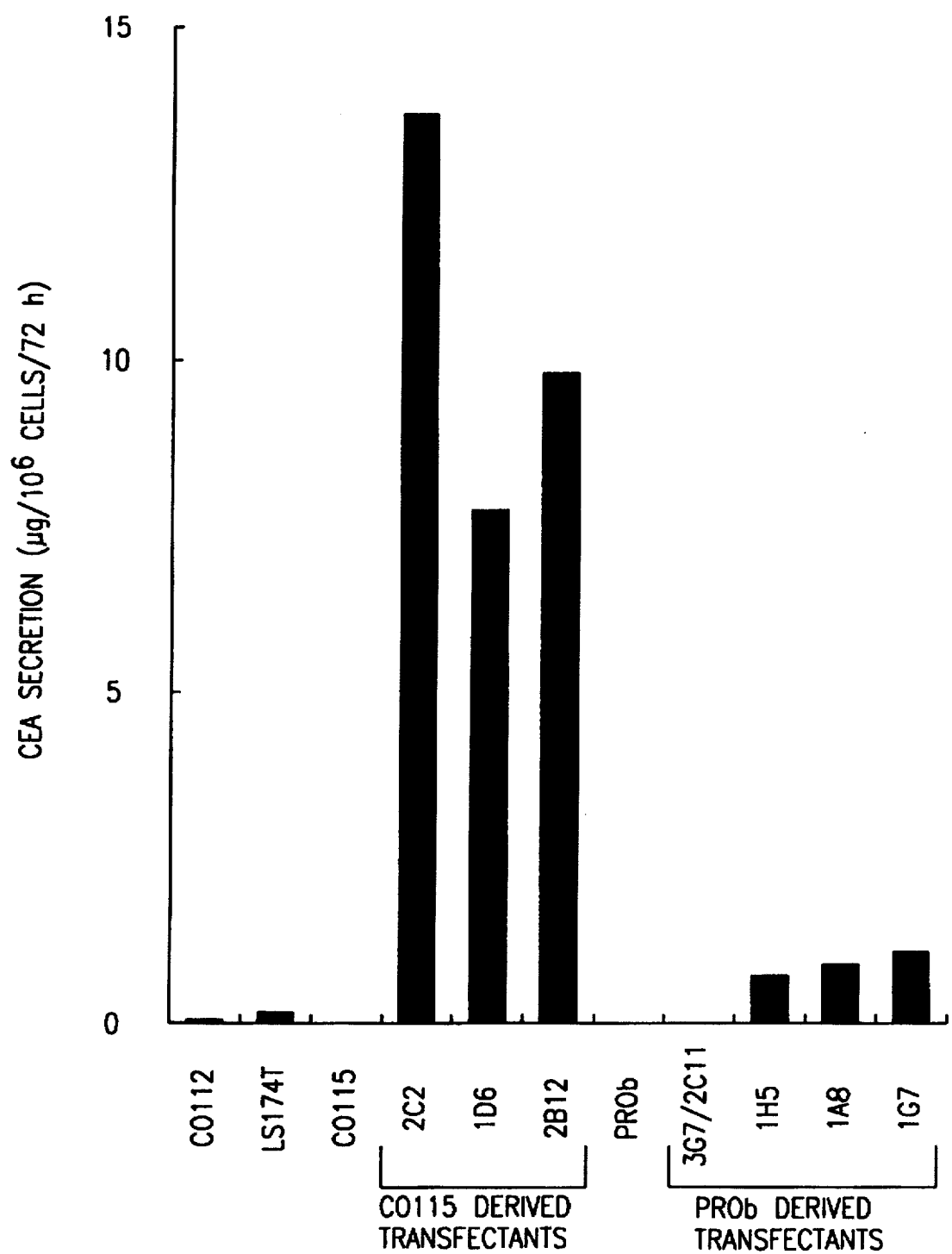
FIG. 2: CEA secretion by different clones and control cell lines. CO115, a CEA-negative clone of a human colon carcinoma cell line; 2C2, 1D6, 2B12, truncated CEA-cDNA CO115 derived transfectants; CO112, LS174T, high CEA-expressing human colon carcinoma cell lines; PROb, a rat colon carcinoma cell line; 1H5, 1A8, 1G7, truncated CEA-cDNA PROb derived transfectants; 3G7/2C11, full-length CEA-cDNA PROb derived transfectants (Pèlegrin et al. [1991], supra).
Figure 3:
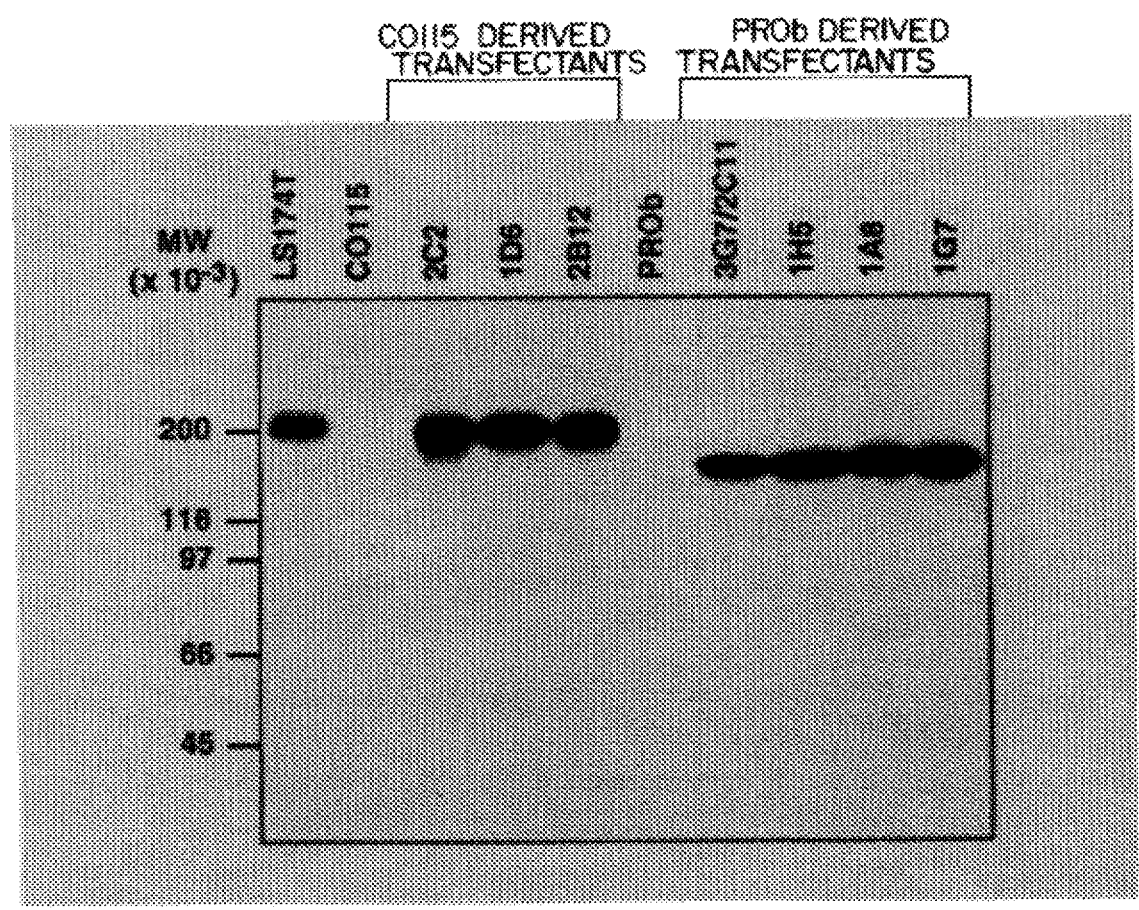
FIG. 3: Western blot analysis of LEA from different clones and control cell lines. Cell culture supernatants were run either directly for the CEA-secreting clones or after treatment of the cells with PI-PLC for the other cells. LS174T, CEA-expressing human colon carcinoma cell line; CO115, CEA-negative clone of human colon carcinoma cell line; 2C2, 1D6, 2B12, truncated CEA-cDNA CO115 derived transfectants; PROb, a rat colon carcinoma cell line; 3G7/2C11, full-length CEA-cDNA PROb derived transfectants (Pèlegrin et al. [1992], supra); 1H5, 1A8, 1G7, truncated CEA-cDNA PROb derived transfectants.
Figure 4:
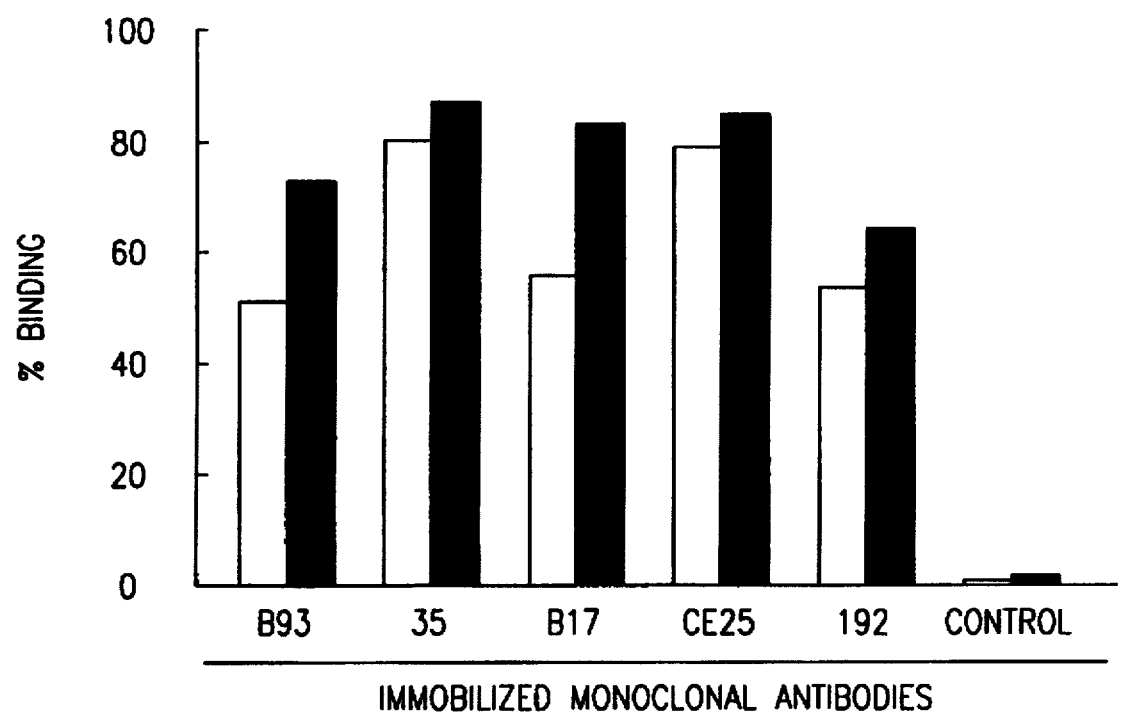
FIG. 4: Binding of $^{125}$I-control CEA (☐) and $^{125}$I-rCEA (■) to immobilized MAbs directed against the different CEA epitopes. About 5 ng CEA were incubated for 16 hours at 25° C. with 5 micrograms of each of the 5 anti-CEA MAbs covalently coupled to Sepharose™.

The present invention comprises a recombinant CEA glycoprotein which lacks the 26 amino acid hydrophobic domain at the C-terminal end of the natural CEA glycoprotein. The CEA glycoproteins of the invention are antigenically indistinguishable from the soluble form of CEA shed from tumor cells since said glycoproteins of the invention still contain all five epitopes generally known as the GOLD 1-5 epitopes (Hammarstrom et at. [1989], supra). The lack of the 26 C-terminal amino acids present in the natural CEA glycoproteins also results in the CEA glycoproteins of the invention being devoid of the ethanolamine which is present at the C-terminus of natural CEA, and also being devoid of the additional amino acids which may be attached to the natural CEA through said ethanolamine. The recombinant CEA glycoprotein of the invention is also free from cross-reactive CEA-like antigens since said glycoprotein is produced in CEA-negative host cells, as described below.

Said recombinant CEA glycoprotein is secreted in high amounts in culture medium from cells transfected with a DNA encoding said recombinant CEA glycoprotein.

The invention also comprises recombinant CEA glycoproteins which are fragments of the recombinant CEA glycoprotein described above and which are:

(a) free from cross-reactive CEA-like antigens;

(b) antigenically indistinguishable from the soluble form of CEA shed from tumor cells; and (c) devoid of the ethanolamine attached to the C-terminal end of said natural CEA and the amino acids which may be attached to said natural CEA through said ethanolamine.

The term "free from cross-reactive CEA-like antigens" means that the recombinant CEA glycoprotein of the present invention is secreted by CEA-negative host cells transformed with a recombinant vector comprising a DNA encoding said recombinant CEA glycoprotein. Because the recombinant CEA glycoprotein is not isolated from tumor extracts, it does not contain the cross-reactive CEA-like antigens usually present in such extracts. Any CEA-negative host cell capable of expressing the CEA glycoprotein of the invention may be used in accordance with the present invention. The CEA-negative character of host cells may be determined by conventional means. Preferably, such a determination is made using anti-CEA monoclonal antibodies, as described infra.

The term "antigenically indistingiushable from the soluble form of CEA shed from tumor cells" means that the recombinant CEA glycoprotein of the present invention is immunologically the same as the natural form of CEA, i.e., comprises all five epitopes generally known as the GOLD 1-5 epitopes (Hammarstrom et al. [1989], supra). Therefore, the invention comprises the above-described fragments so long as the fragments contain all of the GOLD 1-5 epitopes.

The term "being devoid of ethanolamine" means that the recombinant CEA glycoprotein of the present invention lacks the ethanolamine attached to the C-terminus of the natural CEA glycoprotein and the fragment of the PI-G tail attached to the natural CEA glycoprotein through the ethanolamine that may be present in the soluble form of CEA as it is obtainable from untransfected tumor cells, e.g., after sheding from tumor cells or after treatment with a phosphatidylinositol-specific phospholipase. Because the DNA encoding the recombinant CEA glycoprotein of the present invention lacks the sequence coding for the hydrophobic C-terminal tail present in the precursor form of natural CEA glycoprotein, the recombinant CEA glycoprotein of the present invention expressed from this DNA cannot be anchored in the cell membrane. It was found that, quite surprisingly, the lack of the hydrophobic domain in the recombinant CEA glycoprotein of the invention does not affect its transport towards the cell surface in either human or rat carcinoma cells, but only prevents its anchoring to the cell surface.

The preferred recombinant CEA glycoprotein of the present invention has the amino acid sequence of SEQ ID NO: 1.

The present invention also comprises functionally equivalent recombinant CEA glycoproteins having amino acid sequences which are related to SEQ ID NO: 1 by deletions, insertions or substitutions so long as the resulting derivatives are:

(a) free from cross-reactive CEA-like antigens;

(b) antigenically indistinguishable from the soluble form of CEA shed from tumor cells; and (c) devoid of the ethanolamine attached to the C-terminal end of said natural CEA and the amino acids which may be attached to said natural CEA through said ethanolamine.

Especially preferred are recombinant CEA glycoproteins of the invention in which amino acid substitutions have been made. Examples of amino acid substitutions which do not substantially alter the biological and immunological properties of a protein have been described, e.g., by Neurath et al., in "The Proteins", Academic Press, New York (1979), in particular in FIG. 6 at page 14 thereof. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Ash, Leu/Ile, Leu/Val, Ala/Glu, Asp/Gly, and vice versa.

The recombinant CEA glycoprotein of the present invention may be labeled by conventional means with one of the labels known in the art, e.g., by a dye, or by a radioactive, enzymatic, fluorescent or chemiluminescent label. The preferred label is radioactively labeled iodine ($^{125}I$).

The recombinant CEA glycoprotein of the present invention may be used as a standard in any conventional immunoassay for detecting CEA in a biological sample, e.g., a sample of a body fluid. The person skilled in the art is in a position to configure such an immunoassay based on the general knowledge in the field of immuno diagnostics. The use of an enzyme linked immuoassay (ELISA) is preferred. Examples for such immunoassays are described, e.g., in EP-A-346,710. Any conventional enzymes which are useful for an ELISA may be used to label the recombinant CEA glycoprotein of the present invention. Examples of such enzymes include, among others, alkaline phosphatase, β-galactosidase, horseradish peroxidase, glucose-6-phosphate dehydrogenase, 3-phosphoglycerate kinase (PGK).

The present invention also comprises immunoassays for the diagnosis of neoplastic diseases wherein a recombinant CEA glycoprotein of the present invention is used, preferably as a standard in the form of a reagent, wherein said recombinant CEA glycoprotein is mixed with an inert carrier material. Examples of such inert carrier materials are distilled water and buffers, possibly containing stabilizers and other additives generally used in reagents for diagnostic purposes.

The present invention also comprises methods for the preparation of such reagents and the reagents per se, as well as test-kits for the determination of the presence of cancer cells in a biological sample. Such a test-kit comprises in a container a reagent containing the recombinant CEA glycoprotein of the present invention, and, if necessary, an inert carrier material. The test kit may also contain, if necessary, additional reagents such as, e.g., monoclonal or polyclonal CEA antibodies.

The recombinant CEA glycoprotein of the present invention is preferably encoded by a fragment of the cDNA which encodes the complete form of the CEA glycoprotein, wherein said DNA fragment lacks the region coding for the C-terminal hydrophobic tail. The DNA fragment may be obtained by any conventional means. One way to obtain such a DNA fragment is to use suitable restriction endonucleases to cut a cDNA encoding the complete form of CEA directly upstream from the region coding for the hydrophobic tail that is lacking in the recombinant CEA glycoprotein of the present invention. The 3' end of the cDNA is then restored by using a synthetic oligonucleotide duplex which encodes the extra nucleotides which were inadvertently cleaved of by the restriction endonuclease. Preferably said synthetic oligonucleotide duplex also comprises a stop codon, which causes the translation to terminate after the last amino acid residue in the encoded amino acid sequence. The restriction endonuclease EaeI is the most suitable enzyme for preparing the DNA fragment. Unfortunately, this restriction endonuclease cleaves the cDNA encoding CEA at more than one position. In order to overcome this problem, an 800 base pair fragment comprising the 3' end of the CEA cDNA can be isolated by digestion with Bsu36I and XbaI endonucleases, and then cutting the fragment obtained in this way with EaeI separately.

The preferred DNA encoding a recombinant CEA glycoprotein of the present invention, is a DNA having the nucleotide sequence SEQ ID NO: 2.

It is understood that SEQ ID NO: 2 includes the codons coding for the 34 amino acid residue long signal peptide which is also present in the natural form of the gene encoding CEA, which signal peptide sequence is cleaved off during the maturation of the CEA glycoprotein. On the other hand, quite obviously, said DNA sequence does not comprise the codons encoding the C-terminal hydrophobic domain present in the natural form of the gene encoding CEA.

As indicated above, a DNA which encodes a recombinant CEA glycoprotein of the invention can be prepared by using conventional methods of recombinant DNA technology from a cDNA coding for the full-length form of CEA. Such a DNA sequence can also be prepared by any conventional chemical synthesis technique. Alternatively, the DNA sequence may be prepared by combining, by any conventional means, appropriate DNA fragments in such a way that a complete DNA which encodes a recombinant CEA glycoprotein of the invention is obtained.

Because of the degeneracy of the genetic code, it will be understood that there are many potential nucleotide sequences (functional equivalents) that could code for the recombinant CEA glycoprotein having the amino acid sequence of SEQ ID NO: 1. Therefore, the present invention also relates to a functional equivalent of the sequence of SEQ ID NO: 2, which nucleotide sequence encodes a CEA glycoprotein having the amino acid sequence of SEQ ID NO: 1. Such a functionally equivalent nucleotide sequence may readily be prepared by conventional means. For example, such a functionally equivalent nucleotide sequence may be prepared using appropriate synthetic oligonucleotides in primer-directed, site-specific mutagenesis on the exemplary cDNA of this invention [SEQ ID NO: 2], as described by Morinaga Y., Franceschini T., Inouye S. and Inouye M., "Improvement of oligonucleotide-directed site-specific mutagenesis using double-stranded plasmid DNA", *Bio/Technology* 2, 636–639 [1984].

The present invention still further comprises recombinant vectors containing and capable of directing the expression of a DNA encoding a recombinant CEA glycoprotein of the invention in a compatible host cell, and host cells containing such vectors. It should also be understood that the nucleotide sequences of the present invention which are to be inserted into a recombinant vectors may include additional nucleotides, which additional nucleotides are not part of the actual structural gene encoding the recombinant CEA glycoprotein of the present invention, as long as the recombinant vectors containing such additional nucleotides are still capable of directing the production of a recombinant CEA glycoprotein in accordance with the present invention in an appropriate host cell.

The insertion of a DNA encoding a recombinant CEA glycoprotein in accordance with the present invention into a cloning vector may be performed by any conventional means. Such an insertion is easily accomplished when both the DNA and the desired cloning vector have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase. In this way, blunt-end ligation with an enzyme such as T4 DNA ligase may be carried out. Alternatively, any site desired may be produced by ligating nucleotide sequences (linkers) onto the DNA termini. Such linkers may comprise specific oligonucleotide sequences that encode restriction site recognition sequences. The cleaved vector and the DNA coding for the recombinant CEA glycoprotein of the present invention may also be modified by homopolymeric tailing (see Morrow I. F., "Recombinant DNA Techniques", Methods in Enzymology 68, 3–24 [1979]).

Any conventional cloning vector may be used in accordance with the invention so long as the recombinant vector is capable of directing the expression of the recombinant CEA glycoprotein of the invention in a host cell. Many of the cloning vectors known to the person skilled in the art may be used for preparing the recombinant vectors in accordance with the present invention. Such cloning vectors comprise one or more marker activities that may be used to select for desired transformants. Examples for such marker activities are, e.g., neomycin resistance (see Example below), geneticin resistance and methothrexate resistance.

It should be understood that there are many ways to insert a DNA encoding the recombinant CEA glycoprotein of the present invention into a cloning vector. What is essential in this respect is that the recombinant vector is capable of directing the production of the recombinant CEA glycoprotein in an appropriate host cell.

Preferably, the recombinant vectors comprising a DNA having a nucleotide sequence encoding a recombinant CEA glycoprotein of the present invention may be prepared by:

(a) inserting a DNA having a nucleotide sequence encoding the recombinant CEA glycoprotein into a vector;

(b) replicating the said vector in a host cell; and (c) isolating the recombinant vector from the host cell.

The selection of an appropriate host cell is affected by a number of factors known in the art. These factors include, for example, compatibility with the chosen vector, toxicity of proteins encoded by the recombinant vectors, capability to secrete the desired protein, ease of recovery of the desired CEA glycoprotein, expression characteristics, biosafety and costs. A balance of these factors must be considered, and it must be understood that not all hosts will be equally effective for expression of a particular recombinant DNA molecule. The preferred host cells for producing the recombinant CEA glycoprotein of the present invention are CEA-negative cells. Such cells may be screened for by any conventional means. For example, fluorescent activated cell sorting in conjunction with directly fluorescinated anti-CEA monoclonal antibodies may be used to demonstrate that a cell line expresses no CEA and no CEA-crossreactive antigens at the cell surface. ELISA may also be used to demonstrate that the untransfected cell's culture medium contains no CEA or CEA-crossreacting antigens which may interfere in the assay.

Examples of CEA negative cells are human or rat colon carcinoma cells, e.g., the subclone CO115$^{31}$ from the human colon carcinoma cell line CO115 described by Mach et at. (Mach J. P., Carrel S., Merenda C., Sordat B. and Cerottini J. C., "In vivo localization of radiolabelled antibodies to carcinoembryonic antigen in human colon carcinoma grafted into nude mice", Nature 248, 704–706 [1974]; see also Carrel S., Sordat B. and Merenda C., "Establishment of a cell line (Co-115) from a human colon carcinoma transplanted into nude mice", Cancer Res. 36, 3978–3984 [1976]) and the rat colon carcinoma cell line PROb described by Caignard et at. (Caignard A., Martin M. S., Michel M. F. and Martin F., "Interaction between two cellular subpopulations of a rat colonic carcinoma when inoculated to the syngeneic host", Int. J. Cancer 36, 273–279 [1985]). The said subclone CO115$^-$ was shown by fluorescent activated cell sorting using a panel of directly fluorescinated anti-CEA monoclonal antibodies, to express no CEA and no CEA-crossreactive antigens at the cell surface. It was also shown by enzyme linked immunoadsorbent assay that the culture medium from the untransfected CO115$^-$ subclone contains no CEA or CEA-crossreacting antigens which may interfere in the assay.

Various methods for introducing a foreign DNA fragment into a cell are known to the person skilled in the art. Examples of such methods are microinjection, electroporation, transfection and infection with a viral vector. The preferred method for inserting a recombinant cDNA encoding the recombinant CEA glycoprotein of the present invention into a cell is the well-known calcium phosphate method (originally described by Graham F. L. and Van der Eb A. J., "A new technique for the assay of infectivity of human adenovirus 5 DNA", Virology 54, 456–467 [1973]). Geneticin-resistant transfectants can be screened for CEA secretion in the supernatant by an ELISA test using anti-CEA antibodies. Once a transformed host cell is produced, the cell population may be amplified by culturing by conventional means in a culture medium comprising the necessary nutrients under conditions suitable for the growth of the cell population and/or under conditions suitable for high secretion of the recombinant DNA, leading to the production of high amounts of the recombinant CEA glycoprotein of the present invention.

The secreted recombinant CEA glycoprotein of the present invention is secreted into the cell culture medium from which it can be isolated by any conventional means. Preferably, this is done by first removing the cells and cellular debris by low speed centrifugation. The supernatant containing the recombinant CEA glycoprotein of the present invention obtained in this way may then be concentrated by ultrafiltration. Initial separation of the recombinant CEA glycoprotein from the supernatant may be performed by precipitation with salts such as sodium or ammonium sulfate, by ultrafiltration or by other methods well known to those skilled in the art. Further purification may be accomplished by conventional protein purification techniques, including but not limited to gel filtration, ion-exchange chromatography, preparative disc-gel or curtain electrophoresis, isoelectric focusing, low temperature organic solvent fractionation, or countercurrent distribution. Purification can also be carried out by immunoaffinity chromatography.

Thus, the present invention also comprises a method for producing the recombinant CEA glycoprotein defined above, which method comprises:

(a) culturing a host cell containing a recombinant vector comprising a DNA having a nucleotide sequence encoding the said recombinant CEA glycoprotein, such as the DNA having the nucleotide sequence [SEQ ID NO: 2] or an equivalent sequence thereof, under conditions in which the DNA is expressed; and (b) isolating the recombinant CEA glycoprotein produced by the host cell from the culture.

The preferred method for the construction of the recombinant cDNA encoding the CEA fragment of the present invention can be summarized as follows:

In the first step, a suitable vector comprising a cDNA encoding the full length CEA protein, such as the Bluescript™ vector described in the Example below, is digested at a unique site with the Bsu36I endonuclease. The cleaved vector is then dephosphorylated and further digested at a unique site with the XbaI endonuclease to generate two fragments of 0.8 and 4.6 Kb (1 Kb=1'000 base pairs) which are isolated.

In the second step, the 4.6 Kb fragment, containing vector DNA and the 5' part of the CEA cDNA, is ligated into a XbaI site with a synthetic oligonucleotide duplex containing the last 43 base pairs (b.p.) of the third CEA repeat downstream from the EaeI site to the codon of the last amino acid found in the mature protein and further containing a TAG stop codon and a XbaI sticky end.

The third step consists of cleaving the 0.8 Kb fragment referred to above at its unique EaeI site. This resulted in two fragments of about 0.4 Kb each, one fragment consisting of the missing part of the third CEA repeat which was to be retained in the final recombinant cDNA and the other fragment consisting of the hydrophobic tail which should be deleted.

In the fourth step the vector is circularized. Of the two 0.4 Kb fragments obtained in the previous step, only the one containing the third CEA repeat has the proper sticky ends, viz. Bsu36I and XbaI, for the double ligation and circularization of the 4.6 Kb fragment joined to the synthetic duplex mentioned above. The resulting construct may be amplified in a suitable vector such as in a Bluescript™ vector. The correct construction of the vector can be checked by restriction analysis using StyI and EaeI endonucleases. The recombinant cDNA encoding the recombinant CEA glycoprotein of the present invention can then be recloned into a vector suitable for the expression of a cDNA in a eukaryotic cell. An example of such a vector is the eukaryotic expression vector pRc/CMV described in the Example below. The vector pRc/CMV is designed for high level, stable expression of inserted genes under the control of the constitutive CMV promoter. The vector comprises also the bovine growth hormone polyadenylation signal and a neomycin resistance gene which is expressed from the SV40 early promoter. The correctness of the final construct can be verified by restriction analysis. The correctness of the new 3' end of the recombinant cDNA encoding the recombinant CEA glycoprotein of the present invention can be confirmed by sequencing.

The vector comprising the recombinant cDNA encoding the recombinant CEA glycoprotein of the present invention and the neomycin-resistance gene are preferably introduced by using the calcium phosphate method transfection method into a CEA-negative cell, such as, e.g., the subclone from the human colon carcinoma cell line CO115 (Mach J. -P. et al. [1974], supra; Cartel S. et al. [1976], supra) or the rat colon carcinoma cell line PROb (Caignard A. et al. [1985], supra).

Depending on the host cell used for inserting the recombinant cDNA encoding the recombinant CEA glycoprotein of the present invention, the transformed host cells were found to shed about 50 to 100 times more CEA than host cells transformed with a cDNA encoding the full length CEA protein. Thus, e.g., the subclones from the human colon carcinoma cell line CO115 transformed with the recombinant cDNA encoding the recombinant CEA glycoprotein of the present invention were found to secrete about 7.7 to 13.6 micrograms CEA/$10^6$ cells/72 h. Under the same conditions, non-transfected human colon carcinoma cells known to have a high level of CEA expression shed about 50 to 300 times less CEA. More precisely the cell line CO112 (Mach J. -P. et al. [1974], supra) shed about 0.045 micrograms CEA/$10^6$ cells/72 h and the cell line LS174T (Rutzky L. P., Kaye C. I., Siciliano M. J., Chao M. and Kahan B. D., "Longitudinal karyotype and genetic signature analysis of cultured human colon adenocarcinoma cell lines LS180 and LS174T", Cancer Res. 40, 1443–1448 [1980]) shed 0.128 micrograms CEA/$10^6$ cells/72 h).

The PROb rat carcinoma clones transfected with the recombinant cDNA encoding the recombinant CEA glycoprotein of the present invention secreted from 0.61 to 0.99 micrograms CEA/$10^6$ cells/72 h. Selected clones from the same PROb cells transfected with full-length CEA-cDNA shed a maximum of only 0.015 micrograms CEA/$10^6$ cells/72 h (Pèlegrin A., Terskikh A., Hayoz D., Chalandon Y., Olsson N. O., Folli S., Buchegger F., Kromer B., Schwarz K., Martin M., Martin F. and Mach J. P., "Human carcinoembryonic antigen cDNA expressed in rat carcinoma cells can function as target antigen for tumor localization of antibodies in nude rats and as rejection antigen in syngeneic rats", Int. J. Cancer 52, 110–119 [1992]). Thus, the transfection of rat colon carcinoma PROb with a CEA-cDNA lacking the C-terminal domain resulted in a 50 fold higher level of CEA secretion compared to clones from the same cell line transfected with full-length CEA cDNA.

The above results show that there is a difference between the amount of recombinant CEA glycoprotein of the present invention (rCEA) secreted by human cells and rat cells. It has been proposed earlier that both transcriptional and post-transcriptional control mechanisms regulate CEA gene expression in colon carcinomas (Hauck W. and Stanners C. P., "Control of carcinoembryonic antigen gene family expression in a differentiating colon carcinoma cell line, Caco-2", Cancer Res. 51, 3526–3533 [1991]). In view of the identity of the DNA constructs used for transfection, this lower secretion rate of rCEA may be attributed to the differences in post-transcriptional control between the two species.

The size of the CEA expressed by the transfected cells can be analyzed by Western blotting (Towbin, H., Staehelin, T. and Gordon J., "Electrophoretic transfer of proteins from polyacrylamide gels to nitrocellulose sheets: Procedure and some applications", Proc. Natl. Acad. Sci. USA ,76, 4350–4354 [1979]). Such an analysis is performed as follows: Cell culture supernatants are electrophoretically separated on a SDS-polyacrylamide gel, preferably a 7.5–15% linear gradient SDS-polyacrylamide gel. Then, an immunoblot is performed using antibodies recognizing a major epitope on the CEA protein. Preferably a pool of $^{125}$I-labeled anti-CEA monoclonal antibodies (MAbs) is used for such purpose. In a typical example the rCEA cDNA-transfected-CO115 human colon carcinoma exemplified below produced a rCEA of about 200 kDa. This corresponds to the size of the CEA protein produced by human colon carcinoma LS174T. When transfected into the PROb rat colon carcinoma, the same rCEA cDNA produced a rCEA with a lower molecular weight (viz. about 144 kDa) as did the full-length CEA cDNA transfected into the PROb rat carcinoma cells (Pèlegrin et al. [1992], supra).

Epitope characterization of $^{125}$I-labeled, purified rCEA produced by the host cells transformed with the recombinant cDNA encoding the recombinant CEA glycoprotein of the present invention can be performed by any conventional means. Preferably, epitope characterization is performed by testing the binding of the said rCEA to different anti-CEA MAbs coupled to SEPHAROSE™. In typical experiments using human colon carcinoma CO115 cells transformed with a recombinant DNA encoding the recombinant CEA glycoprotein of the present invention and five MAbs directed against the GOLD 1 to 5 epitopes on the CEA molecule (Hammarstrom et al. [1989], supra), binding values ranging from 65% to 88% were found (see Example below). Such binding values compare favorably with those obtained with $^{125}$I-labeled CEA purified from a human tumor.

Thus, the present invention shows that transfection into human and rat carcinoma cells of a recombinant CEA cDNA clone from which the region coding for the hydrophobic C-terminal domain has been deleted, results in an abundant secretion of fully antigenic rCEA molecules into the medium. As mentioned above, CEA is normally anchored to the cell membrane by a PI-G tail, and is only shed into the medium of cultured cells or in the serum of carcinoma patients probably after the cleavage from the membrane by PI-specific phospholipases. The recombinant CEA glycoprotein of the present invention is lacking the C-terminal hydrophobic tail. Therefore, it cannot be PI-G anchored, and is directly secreted into the extracellular space. It was found that the lack of the hydrophobic domain in the CEA glycoprotein does not affect the transport of CEA towards the cell surface in either human or rat carcinomas, but only prevents its anchoring to the cell surface. The recombinant CEA glycoprotein of the present invention is recognized by MAbs directed against the five well characterized epitopes GOLD 1–5.

A Western blot analysis has shown that, surprisingly, the recombinant CEA glycoprotein of the invention secreted from the transfected rat colon carcinoma has a lower molecular weight (about 144 kDa) than a reference CEA isolated from a human colon carcinoma (about 200 kDa). This is in agreement with the observation that the CEA produced by rat colon carcinoma cells transfected with full-length CEA cDNA has also the same "lower" molecular weight after cleavage by PI-PLC (Pèlegrin et at. [1992], supra). CEA molecules with abnormal molecular weights expressed in heterologous cells transfected with a full length CEA gene have been observed in the case of mouse L-cells and chinese hamster ovary cells (Hefta et at. 1990). The molecules identified on L-cells transfected with total human DNA had a lower molecular weight (150 kDa) than those identified on transfected hamster cells (180 kDa). Incomplete glycosylation seems to be responsible for the smaller molecular weight of the CEA molecules expressed by rat colon carcinoma cells transfected with either full length CEA cDNA or truncated CEA DNA of the invention.

The present invention can be more readily understood by reference to the following Example and the Figures described above.

EXAMPLE

Unless otherwise specified, percentages given below for solids in solid mixtures, liquids in liquids, and solids in liquids are on a wt/wt, vol/vol and wt/vol basis, respectively. Furthermore, unless otherwise specified, the suppliers of reagents including the full-length CEA cDNA, as well as the instruments mentioned below are not meant to be mandatory. The skilled person is in a position to select similar reagents or instruments from other suppliers.

Deletion of the Region Coding for the Hydrophobic Tail of CEA

The Bluescript™ (KS+) vector containing full-length CEA cDNA between unique HindIII and XbaI sites (Zimmermann W., Weber B., Ortlieb B., Rudert F., Schempp W., Fiebig H., Shively J. E., yon Kleist S. and Thompson J. A., "Chromosomal localization of the carcinoembryonic antigen gene family and differential expression in various tumors", Cancer Res. 48, 2550–2554 [1988]; Pèlegrin et at. [1992], supra)) was digested with endonuclease Bsu36I (Boehringer, Mannheim, Germany) and dephosphorylated with alkaline phosphatase (Boehringer). A second digestion with XbaI (Pharmacia, Uppsala, Sweden) produced two fragments of 0.8 Kb and 4.6 Kb which were separated and electroeluted from a 1% agarose gel (see FIG. 1, step 1).

Two oligonucleotides (46 b. each), encoding both strands of the last 43 basepairs of the third CEA repeat, viz. JPM1 5'-GGCCGCAATAATTCCATAGTCAAGAGCATCACAG TCTCTGCATAGT-3'[SEQ ID NO: 3] and JPM2 5'-CTAGACTATGCAGAGACTGTGATGCTCTTGACTAT GGAATTATTGC-3'[SEQ ID NO: 4], respectively, were synthesized on a commercial DNA synthesizer. The oligonucleotides were purified by passage through a Sephadex™ NAP-25 column (Pharmacia), lyophylized and dissolved in 10 mM Tris-HCl buffer pH 7.6 containing 0.1 mM EDTA.

After gel purification and annealing, the synthetic oligonucleotides form a synthetic duplex encompassing the 43 b.p. of the third CEA repeat downstream from the EaeI to the codon of the last amino acid found in the mature protein. This was followed by a TAG stop codon and by a XbaI sticky end, which forms the 3' end, while the 5' end had a EaeI sticky end.

The duplex was ligated into the XbaI site with the large 4.6 Kb fragment by overnight incubation at 8° C. in 1 mM ATP (see FIG. 1, step 2). The reaction mixture was separated on a 1% agarose gel in order to purify the 4.6 fragment ligated to the synthetic duplex from the excess of the free duplex form.

The 0.8 Kb fragment was digested with EaeI (Boehringer) (see FIG. 1, step 3) and the DNA mixture was ligated with the 4.6 Kb fragment joined to the synthetic duplex (see FIG. 1, step 4). After phosphorylation of the Bsu36I site with polynucleotide kinase 4 (Pharmacia), the construct was circularized and transfected into the E. coli strain XL1-blue (Stratagene Cloning Systems, La Jolla, Calif.). Individual clones were analyzed by restriction with StyI and EaeI endonucleases. DNA from selected clones was amplified and isolated. Recombinant CEA cDNA was cut out by double digestion with HindIII and XbaI endonucleases and cloned into a pRc/CMV expression vector (Invitrogene, San Diego, Calif.).

Individual clones were further controlled with the restriction endonucleases StyI and EaeI. DNA from selected clones was amplified, isolated and about 200 nucleotides from the 3' end of the recombinant CEA cDNA, including the 46 b.p. region formed by the synthetic duplex, were sequenced using T7 and SP6 primer with a USB Sequencing kit (USB, Cleveland, Ohio).

Cell Cultures and Transfections

The human colon carcinoma cell line CO115 was established according to known procedures (Mach et al. [1974], supra; Cartel et al. [1976], supra). The rat colon carcinoma cell line DHD/K12/TRb, referred to as PROb, is a selected subclone derived from a cell line established from a transplantable colon adenocarcinoma induced by 1,2-dimethylhydrazine in a syngeneic BDIX rat (Martin F., Caignard A., Jeannin J. F., Leclerc A. and Martin M., "Selection by trypsin of two sublines of rat colon cancer cells forming progressive or regressive tumors", Int. J.

*Cancer.* 32, 623–627 [1983]). The PROb subclone has been shown to induce progressive tumors in rats of the Berlin Druckrey IX/Orl (BDIX) strain (Caignard et al. [1985], supra). The human and rat cell lines were maintained in RPMI 1640 and Dulbecco F12 medium, respectively, supplemented with 10% fetal calf serum (FCS). Three micrograms of DNA were precipitated with calcium phosphate (Mammalian Transfection K it, Stratagene, La Jolla, Calif.) and incubated for 16 hours with about $3 \times 10^6$ nonconfluent adherent carcinoma cells in 10 ml of culture medium with 10% FCS. The medium was removed and 10 ml of fresh culture medium were then added. After a further 24-hours incubation, the cells were harvested, distributed into four 96-well microtiter plates and grown for 24 hours before adding the neomycin analog G418 (Gibco, Paisley, Scotland) at a concentration of 200 micrograms/ml. The supernatants from each well were screened by ELISA (Buchegger F., Mettraux C., Accolla R. S., Carrel S. and Mach J. -P., "Sandwich enzyme immunoassay using three monoclonal antibodies against different epitopes of carcinoembryonic antigen (CEA)", *Immunol. Lett.* 5, 85–91 [1982]) for CEA secretion.

Monoclonal Antibodies

MAb B93, 35, B17, and CE25 are specific for CEA; they do not bind to crossreacting antigens nor to granulocytes (Buchegger F., Pèlegrin A., Delaloye B., Bischof-Delaloye A. and Mach J. -P., "$^{131}$-I labeled F(ab')2 fragments are more efficient and less toxic than intact anti-CEA antibodies in radioimmunotherapy of large human colon carcinoma grafted in nude mice", *J. Nucl. Med.*, 31, 1035–1044 [1984]). MAb 192 is an anti-CEA antibody which cross-reacts with non-specific crossreacting antigen (NCA) (Buchegger F., Schreyer M., Carrel S. and Mach J. -P., "Monoclonal antibodies identify a CEA crossreacting antigen of 95 kD (NCA-95) distinct in antigenicity and tissue distribution from the previously described NCA of 55 kD", *Int. J. Cancer*, 33, 643–649 [1984]). Each of the five Mabs (B93, 35, B17, CE25 and 192) reacts specifically with one of the recently identified Gold 1–5 epitopes of the CEA molecule (Hammarstrom et at. [1989], supra).

Assay for CEA Production

An equal number of cells ($5 \times 10^5$) from CEA cDNA transfected human or rat carcinoma clones or from untransfected human colon carcinomas was added to each well of a 24-well culture plate (Falcon, Becton Dickinson, Oxnard, USA) in 10% FCS RPMI medium. After 18 hours, the complete medium was replaced by 1 ml serum-free medium, which markedly decreases cell proliferation without inhibiting CEA secretion. The supernatants were harvested following a further 72 hours incubation. The amount of CEA in the supernatants was determined by an enzyme linked immunoabsorbant assay (ELISA) using 3 anti-CEA MAbs (Buchegger et al. [1982], supra).

CEA Purification and Labeling with $^{125}$I rCEA was affinity purified from serum-free culture supernatant on an immunoabsorbant column consisting of MAb B17 coupled to SEPHAROSE™. Batches of 50 ml serum-free culture supernatant were applied at a rate of 2 ml/hour on a 2 ml SEPHAROSE™ column containing 4 mg of B17 MAb. The bound CEA was eluted from the column with 3M ammonium thiocyanate in $H_2O$ and immediately dialyzed against 0.1M Tris buffer, pH 7.4.

CEA was extracted from liver metastases using the perchloric acid method (Krupey J., Wilson T., Freedman S. O. and Gold P., "The preparation of purified carcinoembryonic antigen of the human digestive system from large quantities of tumour tissue", *Immunochem.* 9, 617–622 [1972]; Fritsche R. and Mach J. P., "Isolation and characterization of carcinoembryonic antigen (CEA) extracted from normal human colon mucosa", *Immunochem.* 14, 119–127 [1977]). Briefly, one volume of tissue was first homogenized in 3 volumes of 0.03M phosphate buffer, pH 7.0 at 4° C. for 10 minutes in a Sorvall, OMNIMIXER (Sorvall, Newton, Conn., USA) at 8.000 rpm. The crude homogenate was extracted with 0.6M perchloric acid for 20 minutes and centrifuged at 10,000 rpm for 10 minutes. The supernatant was dialyzed against deionized water, lyophilyzed, dissolved in Tris buffer and purified by gel filtration on a SEPHADEX™ G-200 column followed by a Sepharose™ 6B column.

Batches of 20 micrograms purified CEA and rCEA were labeled with 1 mCi $^{125}$I using the chloramine T method. The iodine incorporation was about 30–40%. $^{125}$I-labeled CEA and rCEA were further purified by gel filtration on a Sephadex™ G-200 column.

Epitope Characterization

The different epitopes of the CEA molecule were analyzed in a direct binding assay. About 5 ng $^{125}$I-CEA were incubated for 16 hours at 25° C. with 5 micrograms of each of the 5 anti-CEA MAbs coupled to CNBr-SEPHAROSE™ (Pharmacia). The percentage of specific binding was determined by measuring the radioactivity bound to the MAb. The non-specific binding of $^{125}$I-CEA was determined by similar incubation with an irrelevant IgG coupled to Sepharose™.

Western Blot Analysis

Cell culture supernatants from selected transfected clones secreting rCEA were analyzed by Western blot analysis without further treatment. Control untransfected human colon carcinoma cells ($5-10 \times 10^6$) synthesizing membrane-bound CEA were treated with 0.5–1.0 unit of phosphatidylinositol-specific phospholipase C (PI-PLC) (Boehringer Mannheim, Germany) for 1 hour at 37° C. in RPMI medium containing 1 mg/ml BSA and 20 mM EDTA.

Samples of cell culture supernatants containing about 100 ng CEA were run on a 7.5–15% linear gradient SDS-PAGE gel and transferred to a nitrocellulose membrane (Millipore, Bedford, Mass.). Biotinylated SDS-PAGE standards (Bio-Rad, Richmond, Calif.) were used to determine molecular weights. Membranes were incubated overnight with a pool of 4 $^{125}$I-labeled anti-CEA MAbs (35, CE25, B93 and B17) and $^{125}$I-labeled avidin at 4° C. and then subjected to autoradiography.

We claim:

1. A recombinant carcino-embryonic antigen glycoprotein lacking the 26 amino acid hydrophobic domain at the C-terminal end of natural carcino-embryonic antigen glycoprotein and devoid of the ethanolamine attached to the C-terminal end of said natural carcino-embryonic antigen glycoprotein which recombinant glycoprotein comprises the amino acid sequence SEQ ID NO: 1.

2. A reagent for the diagnosis of neoplastic diseases comprising the recombinant carcino-embryonic antigen glycoprotein of claim 1 and an inert carrier material.

3. A test-kit for the diagnosis of neoplastic diseases, which test-kit comprises a container holding the reagent of claim 2.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
    ( A ) LENGTH: 642 amino acids
    ( B ) TYPE: amino acid
    ( C ) STRANDEDNESS: single
    ( D ) TOPOLOGY: unknown ( i i ) MOLECULE TYPE: protein ( i i i ) HYPOTHETICAL: NO ( i i i ) ANTI-SENSE: NO ( v ) FRAGMENT TYPE: C-terminal ( v i ) ORIGINAL SOURCE:
    ( A ) ORGANISM: Homo sapiens ( x i ) SEQUENCE DESCRIPTION: SEQ ID NO: 1:

```
Lys Leu Thr Ile Glu Ser Thr Pro Phe Asn Val Ala Glu Gly Lys Glu
  1               5                  10                  15
Val Leu Leu Leu Val His Asn Leu Pro Gln His Leu Phe Gly Tyr Ser
                 20                  25                  30
Trp Tyr Lys Gly Glu Arg Val Asp Gly Asn Arg Gln Ile Ile Gly Tyr
             35                  40                  45
Val Ile Gly Thr Gln Gln Ala Thr Pro Gly Pro Ala Tyr Ser Gly Arg
     50                  55                  60
Glu Ile Ile Tyr Pro Asn Ala Ser Leu Leu Ile Gln Asn Ile Ile Gln
 65                  70                  75                  80
Asn Asp Thr Gly Phe Tyr Thr Leu His Val Ile Lys Ser Asp Leu Val
                 85                  90                  95
Asn Glu Glu Ala Thr Gly Gln Phe Arg Val Tyr Pro Glu Leu Pro Lys
                100                 105                 110
Pro Ser Ile Ser Ser Asn Asn Ser Lys Pro Val Glu Asp Lys Asp Ala
             115                 120                 125
Val Ala Phe Thr Cys Glu Pro Glu Thr Gln Asp Ala Thr Tyr Leu Trp
    130                 135                 140
Trp Val Asn Asn Gln Ser Leu Pro Val Ser Pro Arg Leu Gln Leu Ser
145                 150                 155                 160
Asn Gly Asn Arg Thr Leu Thr Leu Phe Asn Val Thr Arg Asn Asp Thr
                165                 170                 175
Ala Ser Tyr Lys Cys Glu Thr Gln Asn Pro Val Ser Ala Arg Arg Ser
            180                 185                 190
Asp Ser Val Ile Leu Asn Val Leu Tyr Gly Pro Asp Ala Pro Thr Ile
    195                 200                 205
Ser Pro Leu Asn Thr Ser Tyr Arg Ser Gly Glu Asn Leu Asn Leu Ser
    210                 215                 220
Cys His Ala Ala Ser Asn Pro Pro Ala Gln Tyr Ser Trp Phe Val Asn
225                 230                 235                 240
Gly Thr Phe Gln Gln Ser Thr Gln Glu Leu Phe Ile Pro Asn Ile Thr
                245                 250                 255
Val Asn Asn Ser Gly Ser Tyr Thr Cys Gln Ala His Asn Ser Asp Thr
            260                 265                 270
```

-continued

| | | | | | | | | | | | | | | |
|---|---|---|---|---|---|---|---|---|---|---|---|---|---|---|
| Gly | Leu | Asn 275 | Arg | Thr | Thr | Val | Thr 280 | Thr | Ile | Thr | Val | Tyr 285 | Ala | Glu | Pro |
| Pro | Lys 290 | Pro | Phe | Ile | Thr | Ser 295 | Asn | Asn | Ser | Asn | Pro 300 | Val | Glu | Asp | Glu |
| Asp 305 | Ala | Val | Ala | Leu | Thr 310 | Cys | Glu | Pro | Glu | Ile | Gln 315 | Asn | Thr | Thr | Tyr 320 |
| Leu | Trp | Trp | Val | Asn 325 | Asn | Gln | Ser | Leu | Pro 330 | Val | Ser | Pro | Arg | Leu 335 | Gln |
| Leu | Ser | Asn | Asp 340 | Asn | Arg | Thr | Leu | Thr 345 | Leu | Leu | Ser | Val | Thr 350 | Arg | Asn |
| Asp | Val | Gly 355 | Pro | Tyr | Glu | Cys | Gly 360 | Ile | Gln | Asn | Glu | Leu 365 | Ser | Val | Asp |
| His | Ser 370 | Asp | Pro | Val | Ile | Leu 375 | Asn | Val | Leu | Tyr | Gly 380 | Pro | Asp | Asp | Pro |
| Thr 385 | Ile | Ser | Pro | Ser | Tyr 390 | Thr | Tyr | Tyr | Arg | Pro 395 | Gly | Val | Asn | Leu | Ser 400 |
| Leu | Ser | Cys | His | Ala 405 | Ala | Ser | Asn | Pro | Pro 410 | Ala | Gln | Tyr | Ser | Trp 415 | Leu |
| Ile | Asp | Gly | Asn 420 | Ile | Gln | Gln | His | Thr 425 | Gln | Glu | Leu | Phe | Ile 430 | Ser | Asn |
| Ile | Thr | Glu 435 | Lys | Asn | Ser | Gly | Leu 440 | Tyr | Thr | Cys | Gln | Ala 445 | Asn | Asn | Ser |
| Ala | Ser 450 | Gly | His | Ser | Arg | Thr 455 | Thr | Val | Lys | Thr | Ile 460 | Thr | Val | Ser | Ala |
| Glu 465 | Leu | Pro | Lys | Pro | Ser 470 | Ile | Ser | Ser | Asn | Ser 475 | Lys | Pro | Val | Glu 480 |
| Asp | Lys | Asp | Ala | Val 485 | Ala | Phe | Thr | Cys | Glu 490 | Pro | Glu | Ala | Gln | Asn 495 | Thr |
| Thr | Tyr | Leu | Trp 500 | Trp | Val | Asn | Gly | Gln 505 | Ser | Leu | Pro | Val | Ser 510 | Pro | Arg |
| Leu | Gln | Leu 515 | Ser | Asn | Gly | Asn | Arg 520 | Thr | Leu | Thr | Leu | Phe 525 | Asn | Val | Thr |
| Arg | Asn 530 | Asp | Ala | Arg | Ala | Tyr 535 | Val | Cys | Gly | Ile | Gln 540 | Asn | Ser | Val | Ser |
| Ala 545 | Asn | Arg | Ser | Asp | Pro 550 | Val | Thr | Leu | Asp | Val 555 | Leu | Tyr | Gly | Pro | Asp 560 |
| Thr | Pro | Ile | Ile | Ser 565 | Pro | Pro | Asp | Ser | Ser 570 | Tyr | Leu | Ser | Gly | Ala 575 | Asn |
| Leu | Asn | Leu | Ser 580 | Cys | His | Ser | Ala | Ser 585 | Asn | Pro | Ser | Pro | Gln 590 | Tyr | Ser |
| Trp | Arg | Ile 595 | Asn | Gly | Ile | Pro | Gln 600 | Gln | His | Thr | Gln | Val 605 | Leu | Phe | Ile |
| Ala | Lys 610 | Ile | Thr | Pro | Asn | Asn 615 | Asn | Gly | Thr | Tyr | Ala 620 | Cys | Phe | Val | Ser |
| Asn | Leu 625 | Ala | Thr | Gly | Arg | Asn 630 | Asn | Ser | Ile | Val | Lys 635 | Ser | Ile | Thr | Val 640 |
| Ser | Ala | | | | | | | | | | | | | | |

( 2 ) INFORMATION FOR SEQ ID NO: 2:

( i ) SEQUENCE CHARACTERISTICS:
    ( A ) LENGTH: 2031 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Homo sapiens ( x i ) SEQUENCE DESCRIPTION: SEQ ID NO: 2:

| | | | | | |
|---|---|---|---|---|---|
| ATGGAGTCTC | CCTCGGCCCC | TCCCCACAGA | TGGTGCATCC | CCTGGCAGAG | GCTCCTGCTC | 60 |
| ACAGCCTCAC | TTCTAACCTT | CTGGAACCCG | CCCACCACTG | CCAAGCTCAC | TATTGAATCC | 120 |
| ACGCCGTTCA | ATGTCGCAGA | GGGGAAGGAG | GTGCTTCTAC | TTGTCCACAA | TCTGCCCCAG | 180 |
| CATCTTTTTG | GCTACAGCTG | GTACAAAGGT | GAAAGAGTGG | ATGGCAACCG | TCAAATTATA | 240 |
| GGATATGTAA | TAGGAACTCA | ACAAGCTACC | CCAGGGCCCG | CATACAGTGG | TCGAGAGATA | 300 |
| ATATACCCCA | ATGCATCCT | GCTGATCCAG | AACATCATCC | AGAATGACAC | AGGATTCTAC | 360 |
| ACCCTACACG | TCATAAAGTC | AGATCTTGTG | AATGAAGAAG | CAACTGGCCA | GTTCCGGGTA | 420 |
| TACCCGGAGC | TGCCCAAGCC | CTCCATCTCC | AGCAACAACT | CCAAACCCGT | GGAGGACAAG | 480 |
| GATGCTGTGG | CCTTCACCTG | TGAACCTGAG | ACTCAGGACG | CAACCTACCT | GTGGTGGGTA | 540 |
| AACAATCAGA | GCCTCCCGGT | CAGTCCCAGG | CTGCAGCTGT | CCAATGGCAA | CAGGACCCTC | 600 |
| ACTCTATTCA | ATGTCACAAG | AAATGACACA | GCAAGCTACA | AATGTGAAAC | CCAGAACCCA | 660 |
| GTGAGTGCCA | GGCGCAGTGA | TTCAGTCATC | CTGAATGTCC | TCTATGGCCC | GGATGCCCCC | 720 |
| ACCATTTCCC | CTCTAAACAC | ATCTTACAGA | TCAGGGGAAA | ATCTGAACCT | CTCCTGCCAC | 780 |
| GCAGCCTCTA | ACCCACCTGC | ACAGTACTCT | TGGTTTGTCA | ATGGGACTTT | CCAGCAATCC | 840 |
| ACCCAAGAGC | TCTTTATCCC | CAACATCACT | GTGAATAATA | GTGGATCCTA | TACGTGCCAA | 900 |
| GCCCATAACT | CAGACACTGG | CCTCAATAGG | ACCACAGTCA | CGACGATCAC | AGTCTATGCA | 960 |
| GAGCCACCCA | AACCCTTCAT | CACCAGCAAC | AACTCCAACC | CCGTGGAGGA | TGAGGATGCT | 1020 |
| GTAGCCTTAA | CCTGTGAACC | TGAGATTCAG | AACACAACCT | ACCTGTGGTG | GGTAAATAAT | 1080 |
| CAGAGCCTCC | CGGTCAGTCC | CAGGCTGCAG | CTGTCCAATG | ACAACAGGAC | CCTCACTCTA | 1140 |
| CTCAGTGTCA | CAAGGAATGA | TGTAGGACCC | TATGAGTGTG | GAATCCAGAA | CGAATTAAGT | 1200 |
| GTTGACCACA | GCGACCCAGT | CATCCTGAAT | GTCCTCTATG | GCCCAGACGA | CCCCACCATT | 1260 |
| TCCCCCTCAT | ACACCTATTA | CCGTCCAGGG | GTGAACCTCA | GCCTCTCCTG | CCATGCAGCC | 1320 |
| TCTAACCCAC | CTGCACAGTA | TTCTTGGCTG | ATTGATGGA | ACATCCAGCA | ACACACACAA | 1380 |
| GAGCTCTTTA | TCTCCAACAT | CACTGAGAAG | AACAGCGGAC | TCTATACCTG | CCAGGCCAAT | 1440 |
| AACTCAGCCA | GTGGCCACAG | CAGGACTACA | GTCAAGACAA | TCACAGTCTC | TGCGGAGCTG | 1500 |
| CCCAAGCCCT | CCATCTCCAG | CAACAACTCC | AAACCCGTGG | AGGACAAGGA | TGCTGTGGCC | 1560 |
| TTCACCTGTG | AACCTGAGGC | TCAGAACACA | ACCTACCTGT | GGTGGGTAAA | TGGTCAGAGC | 1620 |
| CTCCCAGTCA | GTCCCAGGCT | GCAGCTGTCC | AATGGCAACA | GGACCCTCAC | TCTATTCAAT | 1680 |
| GTCACAAGAA | ATGACGCAAG | AGCCTATGTA | TGTGGAATCC | AGAACTCAGT | GAGTGCAAAC | 1740 |
| CGCAGTGACC | CAGTCACCCT | GGATGTCCTC | TATGGGCCGG | ACACCCCCAT | CATTTCCCCC | 1800 |
| CCAGACTCGT | CTTACCTTTC | GGGAGCGAAC | CTCAACCTCT | CCTGCCACTC | GGCCTCTAAC | 1860 |
| CCATCCCCGC | AGTATTCTTG | GCGTATCAAT | GGGATACCGC | AGCAACACAC | ACAAGTTCTC | 1920 |
| TTTATCGCCA | AAATCACGCC | AAATAATAAC | GGGACCTATG | CCTGTTTTGT | CTCTAACTTG | 1980 |
| GCTACTGGCC | GCAATAATTC | CATAGTCAAG | AGCATACAG | TCTCTGCATA | G | 2031 |

(2) INFORMATION FOR SEQ ID NO: 3:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Homo sapiens (xi) SEQUENCE DESCRIPTION: SEQ ID NO: 3:

```
GGCCGCAATA ATTCCATAGT CAAGAGCATC ACAGTCTCTG CATAGT                46
```

(2) INFORMATION FOR SEQ ID NO: 4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Homo sapiens (xi) SEQUENCE DESCRIPTION: SEQ ID NO: 4:

```
CTAGACTATG CAGAGACTGT GATGCTCTTG ACTATGGAAT TATTGC                46
```